United States Patent
Patel-Framroze

(10) Patent No.: US 12,286,399 B2
(45) Date of Patent: Apr. 29, 2025

(54) SYNTHESIS OF (R)(+)-2-(4-CHLORO-2-METHYL PHENOXY)PROPANOIC ACID IN HIGH ENANTIOMERIC EXCESS

(71) Applicant: Bomi Patel-Framroze, Portola Valley, CA (US)

(72) Inventor: Bomi Patel-Framroze, Portola Valley, CA (US)

( * ) Notice: Subject to any disclaimer, the term of this patent is extended or adjusted under 35 U.S.C. 154(b) by 41 days.

(21) Appl. No.: 18/102,727

(22) Filed: Jan. 29, 2023

(65) Prior Publication Data

US 2024/0254069 A1   Aug. 1, 2024

(51) Int. Cl.
*C07C 51/09*   (2006.01)

(52) U.S. Cl.
CPC .......... *C07C 51/09* (2013.01); *C07B 2200/07* (2013.01)

(58) Field of Classification Search
None
See application file for complete search history.

(56) References Cited

U.S. PATENT DOCUMENTS

| 4,173,709 A | 11/1979 | Metivier |
| 4,310,689 A | 1/1982 | Eveleens |

OTHER PUBLICATIONS

Amrutkar (Indo American Journal of Pharmaceutical Research, 2018, 1107) (Year: 2018).*

* cited by examiner

*Primary Examiner* — Sudhakar Katakam
*Assistant Examiner* — Jennifer C Sawyer

(57) ABSTRACT

Provided herein is a process to react optical active chloroalkyl acid alkyl ester and substituted phenols in an aromatic solvent in the presence of a catalytic quantity of a quaternary ammonium salt to yield an optically active substituted phenoxy alkyl acid.

7 Claims, No Drawings

SYNTHESIS OF (R)(+)-2-(4-CHLORO-2-METHYL PHENOXY)PROPANOIC ACID IN HIGH ENANTIOMERIC EXCESS

FIELD

The present disclosure relates to a new process for the manufacture of (R)(+)-2-(4-chloro-2-methylphenoxy)propionic acid starting from (S)(−)-2-chloropropionic acid methyl ester and 4-chloro-2-methylphenol using an aromatic solvent and a catalytic quantity of a quaternary ammonium salt, in a high overall yield and high enantiomeric excess.

BACKGROUND (R)(+)-2-(4-chloro-2-methylphenoxy)propionic acid is also known as an agrochemical phenoxy herbicide, mecoprop-p, which is the active (R)(+)-enantiomer of the older racemic herbicide, mecoprop, 2-(4-chloro-2-methylphenoxy)propanoic acid.

In 1951, Thimann, K. V. (Plant Growth Substances p. 21 (1951) described that the dextrorotatory enantiomer (R)(+)-2-(4-chloro-2-methylphenoxy)propionic acid had twice the phytotoxic activity of the racemic acid 2-(4-chloro-2-methylphenoxy)propanoic acid. The earliest preparations of (R)(+)-2-(4-chloro-2-methylphenoxy)propionic acid involved resolution of the racemic acids. (Matell, Arkiv for Kemi 6, 365, 1953) The disadvantages of resolution are complexity and the resultant 50 percent of the wrong isomer which needs to be recycled via racemization.

Metivier and Sauli (GB1114040A) describe the reaction of the sodium salt of optically pure (D)-2-chloropropionic acid ($[\alpha]_D^{22}$=+4° c=10, water) with 2-methylphenol to form an enantiomerically enhanced (D)-2-(2-methylphenoxy)propionic acid ($[\alpha]_D^{22}$=+18.2° c=10, CHCl$_3$) corresponding to approximately 86 percent enantiomeric excess. Repeating this process with 4-chloro-2-methylphenol resulted in (R)(+)-2-(4-chloro-2-methylphenoxy)propionic acid with a similar 89 percent enantiomeric excess ($[\alpha]D22$=+18.3° c=10, CHCl$_3$). They further describe the in situ formation of the sodium salt of (D)-2-chloropropionic acid from the corresponding (S)-2-chloromethyl propionate ($[\alpha]_D^{22}$=−27.8° no solvent) and it's reaction with 4-chloro-2-methylphenol to make enantiomerically enhanced (R)(+)-2-(4-chloro-2-methylphenoxy)propionic acid ($[\alpha]_D^{22}$=+17.7° c=10, CHCl$_3$) corresponding to 81 percent enantiomeric excess. In a later patent (U.S. Pat. No. 4,173,709) the same authors report that this reaction result is surprising since when the reaction is carried out directly with the optically active 2-chloromethyl propionate, the resulting product is a racemic 2-(4-chloro-2-methylphenoxy)propionic acid.

The reported methods to use (S)(+)-methyl-2-chloropropionate to in situ generate the sodium salt of (D)-2-chloropropionic acid result in a maximum of 82 percent enantiomeric excess of (R)(+)-2-(4-chloro-2-methylphenoxy)propionic acid, which is not of suitable optical purity for commercial use. The use of (S)(+)-methyl-2-chloropropionate as the chiral starting material is preferred over the sodium salt of the same acid to make the desired (R)(+)-2-(4-chloro-2-methylphenoxy)propionic acid, since it is easier to prepare at commercial scale, of lower cost, is easier to handle, is a faster reaction with less energy cost and requires less environmentally hazardous conditions.

Eveleens et al (U.S. Pat. No. 4,310,689) describe a process of condensation of the sodium salt of (D)-2-chloropropionic acid and 4-chloro-2-methylphenol in aqueous media to produce the desired (R)(+)-2-(4-chloro-2-methylphenoxy)propionic acid. The process results in 80 percent to 85 percent enantiomeric excess and is extremely sensitive to the total water content which has to be tightly controlled and is difficult to maintain during commercial manufacturing.

Enzyme catalyzed reactions have also been described as methods to produce the desired (R)(+)-2-(4-chloro-2-methylphenoxy)propionic acid. For example, Klibanov et al (EP206436B) describe a process of using a stereospecific lipase to make the key (D)-2-chloropropionic acid intermediate from racemic 2-chloropropionic acid. Amorosa et al (Chirality 20:115-118, 2008) described the used of a *Candida rugosa* lipase enzyme to catalyze the hydrolysis of racemic 2-(4-chlorophenoxy)acetic acid ester in order to obtain an enantiomeric excess of either racemate of 2-(4-chlorophenoxy)acetic acid depending on the cosolvent used.

Consequently, there still exists a need to produce (R)(+)-2-(4-chloro-2-methylphenoxy)propionic acid starting from (S)(−)-methyl-2-chloropropionate and 4-chloro-2-methylphenol, in high enantiomeric excess (ee) using a single step reaction, in a high yield and optical purity which does not require any further purification, does not require recycle of the undesired stereoisomer, and has a low environmental impact.

BRIEF SUMMARY

The present invention describes a reaction of (S)(−)-2-chloropropionic acid methyl ester and 4-chloro-2-methylphenol using an aromatic solvent in the presence of a catalytic quantity of a quaternary ammonium salt cationic surfactant to produce (R)(+)-2-(4-chloro-2-methylphenoxy)propionic acid in greater than 98 percent purity and greater than 94 percent enantiomeric excess ($[\alpha]_D^{22}$>+18.6° c=10, CHCl$_3$)

In some embodiments, the quaternary ammonium salt cationic surfactant is triethyl benzyl ammonium chloride.

In some embodiments, the aromatic solvent is toluene.

In some aspects, the reaction can be carried out by reacting 1 molar equivalent of 4-chloro-2-methylphenol and 1.0 to 1.5 molar equivalent of (S)(−)-2-chloropropionic acid methyl ester in the presence of 1.0-5.0 molar percent of triethyl benzyl ammonium chloride in 950 ml of refluxing toluene per molar equivalent of 4-chloro-2-methylphenol.

In some aspects, the reaction is completed within 2 hours.

In some aspects, the resultant (R)(+)-2-(4-chloro-2-methylphenoxy)propionic acid requires no additional purification or fractionation step.

DETAILED DESCRIPTION

Before describing the present invention in detail, it is to be understood that the terminology used herein is for the purpose of describing particular embodiments only, and is not intended to be limiting.

In accordance with the present invention, there is provided a process to produce the agrochemical (R)(+)-2-(chloro-2-methylphenoxy)propionic acid with a greater than 94% enantiomeric excess in a cost effective manner, with high yields and no purification or recycle of materials required.

Thus the method described herein uses the hitherto unknown use of triethyl benzyl ammonium chloride as a catalyst for the stereospecific condensation of 4-chloro-2-methylphenol with (S)(−)-2-chloropropionic acid methyl ester in toluene at 110° C. to form the desired (R)(+)-2-(4- chloro-2-methylphenoxy)propionic acid in greater than 94 percent enantiomeric excess, greater than 98% purity by chromatographic analysis and greater than 90 percent overall yield as shown in Example 1.

As can be further seen in Example 2, carrying out the identical reaction of Example 1 in the absence of the triethyl benzyl ammonium chloride as the catalyst results in a significant loss of optical purity of the resultant (R)(+)-2-(4-chloro-2-methylphenoxy)propionic acid, with an enantiomeric excess 82 percent.

Example 3 shows that toluene in Example 1 can be substituted with another aromatic solvent, xylene in Example 1 with similar enantiomeric excess results as seen in Example 1.

Example 4 shows that triethyl benzyl ammonium chloride in Example 1 can be substituted with a different quaternary ammonium chloride compound, N-decyl dimethyl benzyl ammonium chloride as the catalyst with similar enantiomeric excess and purity results as seen in Example 1.

Example 5 shows that substituting the aromatic solvent in Example 1 with a non-aromatic solvent, ethanol, results in racemic (R)(+)-2-(4-chloro-2-methylphenoxy)propionic acid which is a total loss of optical purity.

Finally Example 6 shows that carrying out Example 1 without any solvent also results in racemic (R)(+)-2-(4-chloro-2-methylphenoxy)propionic acid.

This new method provides: (i) for the use of commercially preferable (S)(−)-2-chloropropionic acid methyl ester as an optically pure reagent; (ii) for production of the desired (R)(+)-2-(4-chloro-2-methylphenoxy)propionic acid in very high enantiomeric excess and purity; (iii) for no recycle of any undesired compounds; (iv) for no additional purification requirements prior to further use.

It will be clear to those skilled in the art that modifications can be made to the process described herein without departing from the inventive concept set forth in our claims below.

Example 1

Add 200 ml of toluene, 30 grams of 4-chloro-3-methylphenol and 30 grams of sodium hydroxide flakes into an appropriately sized glass vessel, raise the temperature to 50 degrees centigrade and stir for 15 minutes. Add 1.5 grams of triethyl benzyl ammonium chloride, 40 grams of (S)(−)-2-chloropropionic acid methyl ester slowly over 1 hour and stir for an additional 1 hour. Raise the temperature slowly and remove the water and methanol mix during reflux. Cool to 30 degree centigrade, add 150 ml of water and adjust the pH to 7 with 30% hydrochloric acid. Settle and remove the aqueous phase, add 30% hydrochloric acid to bring the pH between 1 and 2 and stir for 30 minutes. Add 100 ml of dichloromethane, stir for 10 minutes, settle and separate the organic layer. Distill off the dichloromethane, add 50 ml of methanol and stir to solubilize and add into a beaker containing 200 ml of water to obtain a solid. Filter and dry at 50 degree centigrade to yield 40.5 grams of (R)(+)-2-(4-chloro-2-methylphenoxy)propionic acid. ($[\alpha]_D^{22}$=+18.7° c=10, $CHCl_3$) (m.p.=95-96° C.; 95.9% enantiomeric excess optical purity by chiral HPLC; 98.6% purity by reverse phase HPLC area percent).

Example 2

Add 200 ml of toluene, 30 grams of 4-chloro-3-methylphenol and 30 grams of sodium hydroxide flakes into an appropriately sized glass vessel, raise the temperature to 50 degrees centigrade and stir for 15 minutes. Add 40 grams of (S)(−)-2-chloropropionic acid methyl ester slowly over 1 hour and stir for an additional 1 hour. Raise the temperature slowly and remove the water and methanol mix during reflux. Cool to 30 degree centigrade, add 150 ml of water and adjust the pH to 7 with 30% hydrochloric acid. Settle and remove the aqueous phase, add 30% hydrochloric acid to bring the pH between 1 and 2 and stir for 30 minutes. Add 100 ml of dichloromethane, stir for 10 minutes, settle and separate the organic layer. Distill off the dichloromethane, add 50 ml of methanol and stir to solubilize and add into a beaker containing 200 ml of water to obtain a solid. Filter and dry at 50 degree centigrade to yield 34.1 grams of (R)(+)-2-(4-chloro-2-methylphenoxy)propionic acid. (m.p.=87-94° C.; 68.1% enantiomeric excess optical purity by chiral HPLC; 90.8% purity by reverse phase HPLC area percent).

Example 3

Add 200 ml of xylene, 30 grams of 4-chloro-3-methylphenol and 30 grams of sodium hydroxide flakes into an appropriately sized glass vessel, raise the temperature to 50 degrees centigrade and stir for 15 minutes. Add 1.5 grams of triethyl benzyl ammonium chloride, 40 grams of (S)(−)-2-chloropropionic acid methyl ester slowly over 1 hour and stir for an additional 1 hour. Raise the temperature slowly and remove the water and methanol mix during reflux. Cool to 30 degree centigrade, add 150 ml of water and adjust the pH to 7 with 30% hydrochloric acid. Settle and remove the aqueous phase, add 30% hydrochloric acid to bring the pH between 1 and 2 and stir for 30 minutes. Add 100 ml of dichloromethane, stir for 10 minutes, settle and separate the organic layer. Distill off the dichloromethane, add 50 ml of methanol and stir to solubilize and add into a beaker containing 200 ml of water to obtain a solid. Filter and dry at 50 degree centigrade to yield 36.3 grams of (R)(+)-2-(4-chloro-2-methylphenoxy)propionic acid. (m.p.=93-94° C.; 94.3% enantiomeric excess optical purity by chiral HPLC; 97.8% purity by reverse phase HPLC area percent).

Example 4

Add 200 ml of toluene, 30 grams of 4-chloro-3-methylphenol and 30 grams of sodium hydroxide flakes into an appropriately sized glass vessel, raise the temperature to 50 degrees centigrade and stir for 15 minutes. Add 1.5 grams of N-decyl dimethyl benzyl ammonium chloride, 40 grams of (S)(−)-2-chloropropionic acid methyl ester slowly over 1 hour and stir for an additional 1 hour. Raise the temperature slowly and remove the water and methanol mix during reflux. Cool to 30 degree centigrade, add 150 ml of water and adjust the pH to 7 with 30% hydrochloric acid. Settle and remove the aqueous phase, add 30% hydrochloric acid to bring the pH between 1 and 2 and stir for 30 minutes. Add 100 ml of dichloromethane, stir for 10 minutes, settle and separate the organic layer. Distill off the dichloromethane, add 50 ml of methanol and stir to solubilize and add into a beaker containing 200 ml of water to obtain a solid. Filter and dry at 50 degree centigrade to yield 40.9 grams of (R)(+)-2-(4-chloro-2-methylphenoxy)propionic acid. (m.p.=94-95° C.; 95.5% enantiomeric excess optical purity by chiral HPLC; 98.4% purity by reverse phase HPLC area percent).

Example 5

Add 200 ml of ethanol, 30 grams of 4-chloro-3-methylphenol and 30 grams of sodium hydroxide flakes into an appropriately sized glass vessel, raise the temperature to 50 degrees centigrade and stir for 15 minutes. Add 1.5 grams of triethyl benzyl ammonium chloride, 40 grams of (S)(−)-2-chloropropionic acid methyl ester slowly over 1 hour and stir for an additional 1 hour. Raise the temperature slowly and remove the water and methanol mix during reflux. Cool to 30 degree centigrade, add 150 ml of water and adjust the pH to 1 with 30% hydrochloric acid and stir for 30 minutes. Add 100 ml of dichloromethane, stir for 10 minutes, settle and separate the organic layer. Distill off the dichloromethane, add 50 ml of methanol and stir to solubilize and add into a beaker containing 200 ml of water to obtain a solid. Filter and dry at 50 degree centigrade to yield 29 grams of (R)(+)-2-(4-chloro-2-methylphenoxy)propionic acid. (m.p.=90-93° C.; 52.2% enantiomeric excess optical purity by chiral HPLC; 95.7% purity by reverse phase HPLC area percent).

Example 6

Add 137 ml of 50% sodium hydroxide solution and 148 grams of 4-chloro-2-methylphenol into an appropriately sized glass vessel and heat to 90 degrees centigrade. Add 118 grams of (S)(−)-2-chloropropionic acid methyl ester slowly over 30 minutes and keep adding sodium hydroxide as required to maintain the pH between 11 and 11.2 and stir for 2 hours. Adjust the pH to 1 with 30% hydrochloric acid and stir for 30 minutes. Add 100 ml of dichloromethane, stir for 10 minutes, settle and separate the organic layer. Distill off the dichloromethane, add 50 ml of methanol and stir to solubilize and add into a beaker containing 200 ml of water to obtain a solid. Filter and dry at 50 degree centigrade to yield 38.1 grams of (R)(+)-2-(4-chloro-2-methylphenoxy) propionic acid. (m.p.=90-96° C.; 53.9% enantiomeric excess optical purity by chiral HPLC; 90.6% purity by reverse phase HPLC area percent).

What is claimed is:

1. A process of making an optically active substituted phenoxy alkyl acid comprising reacting an optically active chloroalkyl acid alkyl ester with a substituted phenol in an aromatic solvent in the presence of a catalytic quantity of a trialkyl benzyl ammonium halide salt.

2. The process according to claim 1, wherein in the process of making an optically active substituted phenoxy alkyl acid comprising reacting an optically active chloroalkyl acid alkyl ester with a substituted phenol in an aromatic solvent in the presence of a catalytic quantity of a trialkyl benzyl ammonium halide salt, the optically active chloroalkyl acid alkyl ester is (S)(−)-2-chloropropionic acid methyl ester, the substituted phenol is 4-chloro-2-methylphenol and the optically active substituted phenoxy alkyl acid is (R)(+)-2-(4-chloro-2-methylphenoxy) propionic acid with an optical rotation of $[\alpha]D22 > +18.6°$.

3. The process according to claim 2 wherein the trialkyl benzyl ammonium halide is triethyl benzyl ammonium chloride.

4. The process according to claim 2 wherein the aromatic solvent is toluene.

5. The process according to claim 2 wherein the (S)(−)-2-chloropropionic acid methyl ester and 4-chloro-2-methylphenol are reacted in 1.5:1 molar quantities.

6. The process according to claim 3 wherein the triethyl benzyl ammonium chloride concentration in the reaction is between 1.0 and 5.0 mole percent of the 4-chloro-2-methylphenol.

7. The process according to claim 2, wherein the reaction temperature is between 100° C. and 145° C.

* * * * *